United States Patent [19]

Woodford

[11] 4,294,238
[45] Oct. 13, 1981

[54] LOWER LIMB MUSCLE AID DEVICE

[75] Inventor: Thomas J. Woodford, Benton Harbor, Mich.

[73] Assignee: Stephen C. Small, Benton Harbor, Mich. ; a part interest

[21] Appl. No.: 77,600

[22] Filed: Sep. 21, 1979

[51] Int. Cl.³ .............................................. A61F 3/00
[52] U.S. Cl. ...................................... 128/80 G; 2/22; 272/70; 272/96
[58] Field of Search ................. 2/22, 16, 2; 128/80 G; 272/70, 96

[56] References Cited

U.S. PATENT DOCUMENTS

| | | | |
|---|---|---|---|
| 440,684 | 11/1890 | Yagn | 128/80 G |
| 807,908 | 12/1905 | Bradstreet | 128/80 G |
| 1,548,711 | 8/1925 | Cooper | 128/80 G |
| 1,553,874 | 9/1925 | Nivens | 128/80 G |
| 1,562,294 | 11/1925 | Cooper | 128/80 G |
| 1,608,032 | 11/1926 | McNabb | 128/80 G |
| 3,295,517 | 1/1967 | Stevens | 128/80 G |
| 3,473,527 | 10/1969 | Spiro | 128/80 G X |
| 3,506,000 | 4/1970 | Baker | 128/80 G X |
| 3,945,046 | 3/1976 | Stromgren | 2/22 |
| 4,065,814 | 1/1978 | Fox | 128/80 G X |
| 4,089,064 | 5/1978 | Chandler | 2/2 |

Primary Examiner—H. Hampton Hunter
Attorney, Agent, or Firm—Wegner, Stellman, McCord, Wood & Dalton

[57] ABSTRACT

A device for assisting and relaxing a user's leg muscles in and after physical activities, such as jogging. The device includes an elastic strap which extends from under the sole of the user's foot upwardly around the heel thereof to the back of the knee. Securing straps are provided at the lower end of the elastic strap for encircling the waist of the user's foot to secure the lower end of the elastic strap thereto. Securing straps are provided at the upper end of the elastic strap for encircling the user's leg adjacent the knee for securing the upper end of the elastic strap thereto with the elastic strap being urged against the rear of the calf of the user's leg for relaxing and relieving fatigue and tension in the user's leg muscles. The elastic strap further provides a biasing of the user's foot for assisting the leg muscles providing inversion about the subtalar axis during activities, such as jogging.

10 Claims, 3 Drawing Figures

LOWER LIMB MUSCLE AID DEVICE

BACKGROUND OF THE INVENTION

1. Field of the Invention

This invention relates to devices for assisting and relaxing muscles of a user's lower limbs.

2. Description of the Prior Art

A number of apparatuses and devices have been developed for facilitating physical activity, such as walking, running, and jumping, and for providing support of a user's lower limbs and, in particular, the joints thereof. One example of such an apparatus is shown in U.S. Pat. No. 440,684 of Nicholas Yagn. The apparatus shown therein includes a compressed gas holder which is connected in combination with a plurality of springs so as to minimize the exertion on the part of the wearer in activities such as walking, running and jumping.

Herbert J. Bradstreet shows an exercising device in U.S. Pat. No. 807,908, including elastic straps extending from the feet upwardly and over the user's shoulders, with elastic straps extending across the user's chest and back and connected to the straps extending up from the feet. The Bradsheet device is designed to exert strain or resistance in opposition to the movements of the various members of the user's body and, thus, serve as a means for developing the muscles in connection with ordinary activities, such as raising the user's hat to bow, raising his arm, stooping, writing, walking, etc.

John J. Cooper shows a leg and foot developer in U.S. Pat. No. 1,548,711 for restoring lost functions in muscles of the hips, legs and feet. The Cooper device subjects the muscles and tendons of the hips, legs and feet to a resistance in walking to bring about a control of defective muscles and to activate the muscles for producing improved blood circulation.

An elastic rubber back support is shown in U.S. Pat. No. 1,533,874 of James H. Nivens wherein a foot sling is connected at the opposite sides of the user's foot to leg bands extending upwardly therefrom to securing means secured about the calf of the user's leg.

Another form of leg booster for relieving body fatigue is shown in U.S. Pat. No. 3,295,517 of Couvaris J. Stevens. The device includes straps extending downwardly from a vest which is worn on the user's chest and back. The lower end of the straps extend downwardly from the hips of the user to the outer sides of the angles. Auxiliary elastic cross straps are secured to the vertical straps and adjustably encircle the legs of the wearer above and below the knees to stabilize the vertical main straps. As shown in FIG. 1 of the Stevens' patent, the vertical straps extend along the sides of the user and, as seen in FIG. 2, the lower knee securing straps are disposed above the calf of the leg so as to leave the calf effectively unsupported.

Irving Spiro, in U.S. Pat. No. 3,473,527, shows an orthopedic knee support including stiffening members and Velcro fastening means for adjustably securing the support above and below the knee.

Jack R. Baker shows, in U.S. Pat. No. 3,506,000, an ankle support having a body member extending about the achilles' tendon at the back of the user's foot and along the inside and outside of the foot. The device further includes stretchable straps passing under the arch of the foot and over the instep in opposite directions and then about the leg in opposite directions. The straps include means for holding them in the overlapping position.

Lawrence T. Stromgren shows, in U.S. Pat. No. 3,945,046, a flexible knee support somewhat similar to the Spiro knee support discussed above.

A one-piece elastic body suit is disclosed by Edgar N. Fox in U.S. Pat. No. 4,065,814 and includes a plurality of elastic band members disposed between inner and outer layers of the suit and includes a triangularly shaped strap member for receiving the foot of the user. When the suit is worn, the vertical band members are placed under tension by the downward pulling exerted by the feet on the triangular strap member for exerting pressure on different muscles of the body, including the leg, back and shoulder muscles of the body.

In U.S. Pat. No. 4,089,064, Franklin W. Chandler, Jr. shows a protective athletic pants hose including a support for the knee joint. The device includes an attachment from the knee grip to the waist belt thereof for providing transferring of load from the knee area to the waist of the user. The device further includes an attachment from the lower band of the knee grip to a stocking end portion of the toe cap thereof to provide the coordinated functioning of the knee grip with the action of the foot.

SUMMARY OF THE INVENTION

The present invention comprehends an improved device for assisting and relaxing the muscles of a user's lower limbs in and after physical activities, such as jogging and the like.

The device is advantageously adapted for use by persons who, by virtue of general weakness or age, have limited ability to engage in exercising activities, such as jogging or the like. Thus, the device of the present invention provides a highly meritorious functioning in extending the benefits of such exercising activities to a large number of people who would not normally be able to engage in such beneficial activities.

More specifically, the invention comprehends the provision of such a device which includes an elastic strap which is urged against the back of the user's leg calf muscles by an attachment of an upper end of the strap to the leg adjacent the knee and a lower end of the strap to the underside of the user's foot.

The strap may comprise an adjustable elastic strap so as to permit the device to be fitted to the individual user for optimum development of assisting and relaxing pressure against the user's calf muscles.

The elastic strap may extend downwardly around the heel to the arch of the user's foot and may be secured thereto by straps encircling the waist of the user's foot.

The means for securing the upper end of the elastic strap to the user's leg adjacent the knee may comprise straps encircling the leg. In the illustrated embodiment, a pair of such straps are provided, one of which is arranged to encircle the leg above the knee and the other of which is arranged to encircle the leg below the knee.

The device may be formed substantially fully of fabric material with the means for securing the different strap portions comprising a releasable self-holding fabric material, such as Velcro material.

When the device is utilized in connection with running activities, such as jogging, the action thereof causes the muscle action to be somewhat similar to that in downhill jogging.

The muscle assisting and relaxing device of the present invention is extremely simple and economical of construction while yet providing the highly desirable features discussed above.

BRIEF DESCRIPTION OF THE DRAWING

Other features and advantages of the invention will be apparent from the following description taken in connection with the accompanying drawing wherein.

DESCRIPTION OF THE PREFERRED EMBODIMENT

Figure 1:
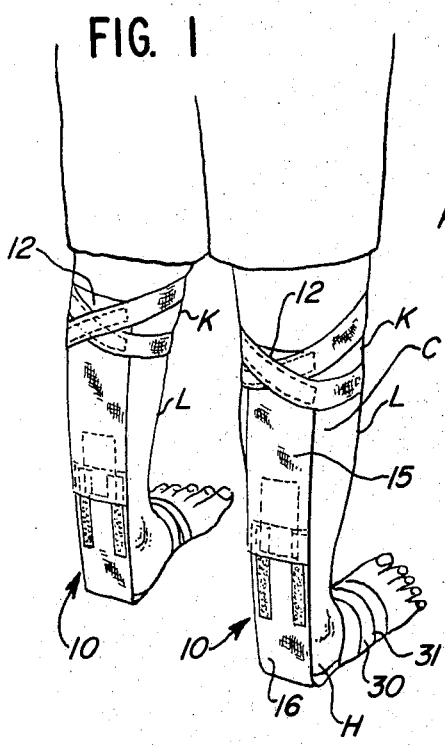
FIG. 1 is a fragmentary rear view of a person provided with a pair of devices embodying the invention installed on his lower limbs.

In the exemplary embodiment of the invention as disclosed in the drawing, a device generally designated 10 is shown to comprise a device for assisting and relaxing the muscles of a user's leg, such as legs L, as illustrated in FIG. 1. The devices 10 for use with each of the user's legs are identical and, thus, the description of the device will be limited to a single such device, herefollowing.

Figure 3:
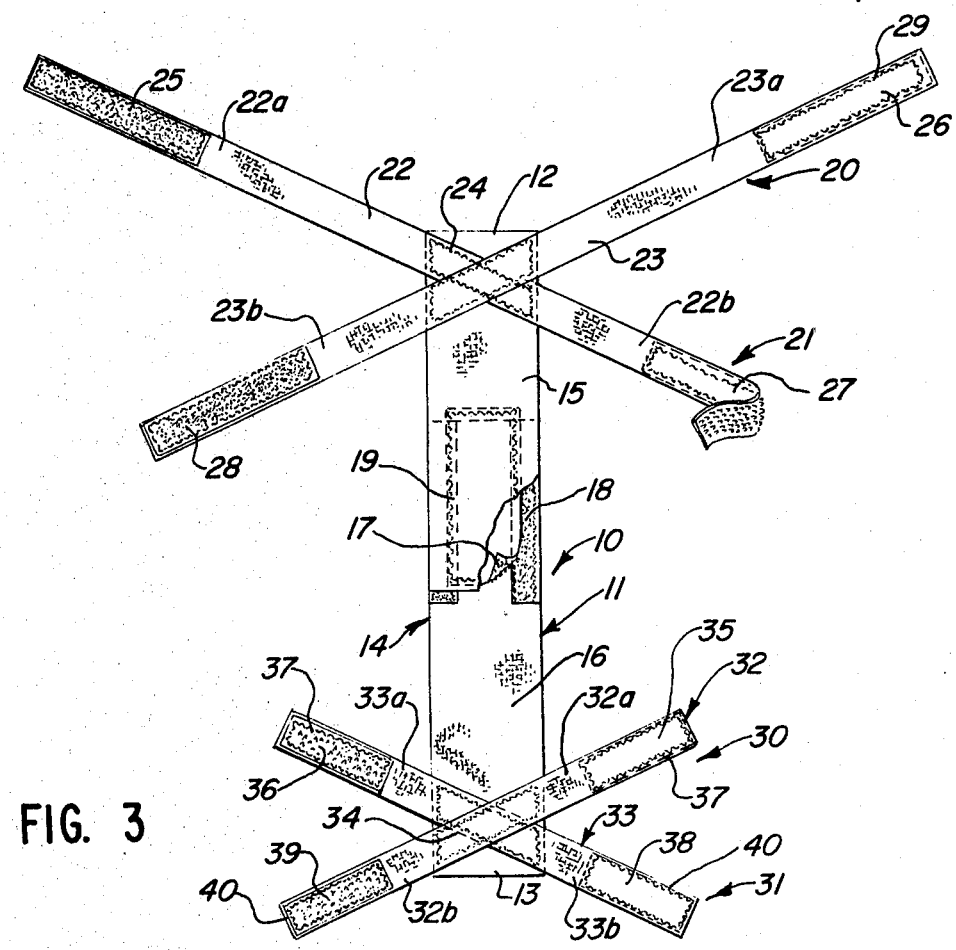
FIG. 3 is a plan view of the device with portions broken away to facilitate illustration of different portions thereof.

As illustrated in FIG. 3, device 10 includes a strap member generally designated 11 having a top end 12, a bottom end 13, and a midportion generally designated 14. The invention comprehends that at least the midportion 14 be elastic and, in the illustrated embodiment, the entire strap member 11 is formed of an elastic material.

As shown in FIG. 3, the strap member may comprise an upper portion 15 and a lower portion 16 which may be adjustably secured in overlapped relationship by a releasable self-holding fabric 17 on upper portion 15 and a complementary releasable self-holding fabric 18 on lower portion 16, which, when pressed together, releasably secure the strap in an adjusted length disposition. Illustratively, the fabric portions 17 and 18 may comprise conventional Velcro patches suitably secured to the strap portions 15 and 16 as by stitching 19, as shown in FIG. 3.

Figure 2:
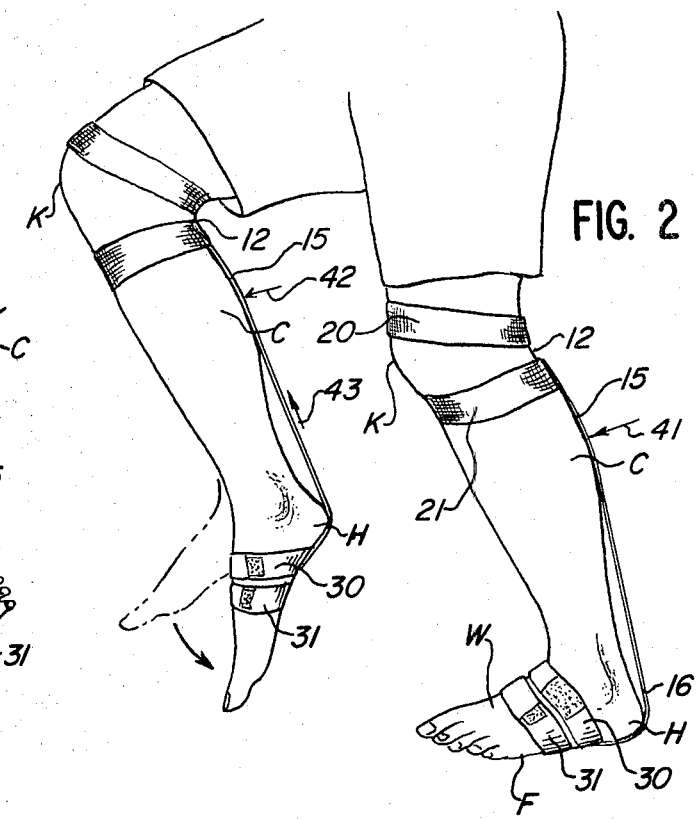
FIG. 2 is a fragmentary side elevation thereof illustrating the action of the device as in a jogging activity.

Upper end 12 of the strap member 11 is secured to the rear of the user's leg behind the knee joint K, as shown in FIGS. 1 and 2. The means for securing the strap end 12 may comprise an upper securing band means generally designated 20 and a lower securing band means generally designated 21. Band means 20 and 21, in the illustrated embodiment, are defined by a pair of elastic straps 22 and 23, which are secured to the elastic strap end 12 in crossed relationship by suitable securing means, such as stitching 24. The upper end 23a of strap 23 and the upper end 22a of strap 22 cooperate with each other to define the upper securing band means 20. Similarly, the lower end 22b of the strap 22 and the lower end 23b of strap 23 cooperate with each other to define the lower securing band means 21. As shown in FIG. 3, strap ends 22a and 23a are provided with complementary releasable self-holding fabric portions 25 and 26, respectively, and strap means 22b and 23b are provided with similarly complementary releasable self-holding fabric portions 27 and 28, respectively. Portions 25, 26, 27 and 28 may comprise conventional Velcro fabric portions and may be secured to the strap end portions by suitable means, such as stitching 29.

As shown, each of the securing band elements has a length suitable to extend cooperatively about the user's leg with band portions 22a and 23a cooperatively extending about the user's leg above the knee joint K and band portions 22b and 23b extending about the user's leg below the knee joint K. The Velcro fastening means permits the user to adjust the tightness of the securing straps so as to provide a comfortable but firm securing of the top end 12 of the elastic strap member 11 to the user's leg at the rear of the knee joint, as discussed above.

As further shown in FIG. 3, the bottom end 13 of the elastic strap member 11 is provided with an upper securing band means 30 and a lower securing band means 31 generally similar to securing band means 20 and 21 but of shorter length for use in encircling the waist portion W of the user's foot F.

As shown in FIG. 3, securing band means 30 and 31 are defined by a pair of elastic straps 32 and 33 secured to strap end 13 in cross relationship by suitable means, such as stitching 34. Upper securing band means 30 is defined by an upper end portion 32a of strap 32 and an upper end portion 33a of strap 33, which end portions are provided with complementary releasable self-holding fabric portions 35 and 36, illustratively comprising Velcro fabric patches secured thereto by suitable means, such as stitching 37.

Lower securing band means 31 is defined by a lower end portion 33b of strap 33 and a lower end portion 32b of strap 32, which are respectively provided with releasable self-holding fabric portions comprising Velcro patches 38 and 39, respectively, which may be secured to the end portions 33b and 32b by suitable means, such as stitching 40.

Thus, Velcro patches 35 and 36 cooperate in providing releasable securing means for securing the securing band means 30 and 31 about the waist W of the user's foot F, as illustrated in FIG. 2.

Elastic strap member 11 and securing straps 22, 23, 32, and 33 may be formed of similar longitudinally extensible resilient fabric. The Velcro patches may be suitably selectively colored for facilitated manipulation in effecting the desired securing of the securing bands about the user's leg and foot portions. Thus, illustratively, the Velcro portions 25 and 26 may be colored red, the Velcro portions 27 and 28 may be colored blue, the Velcro portions 35 and 36 may be colored red and the Velcro portions 38 and 39 may be colored blue.

As illustrated in FIGS. 1 and 2, the device 10 is installed on the user's lower limb with the top end 12 of strap member 11 secured to the back of the user's knee K by the securing band means 20 and 21 and with the lower end 13 of strap 11 secured to the sole of the user's foot by the securing band means 30 and 31.

Desired tension in the strap member 11 may be obtained by suitably facially engaging the Velcro fabric portions 17 and 18 so as to secure the strap portions 15 and 16 in overlapped relationship, as seen in FIGS. 1 and 3, causing the strap member 11 to be urged against the calf C of the user's leg. Further, as seen in FIGS. 1 and 2, the lower portion 16 of strap member 11 is turned about the rear of the user's heel H and, thus, tends to bias the user's foot downwardly about the subtalar axis of the user's foot when the foot is raised from the ground, as illustrated in FIG. 2. As further shown in FIG. 2, strap portion 15 bears against the calf C with an increased pressure illustrated by the arrow 41 when the foot F is brought to the normal forwardly extending disposition as when placed on the subjacent ground surface. In the elevated disposition of the user's foot, as illustrated in FIG. 2, a smaller force is applied by the strap portion 15 to the user's calf muscle as exemplified by the arrow 42, and at the same time, a force as exemplified by the arrow 43 is directed upwardly toward the user's calf toward the user's heel H to provide the desirable assist in the pivoting of the user's foot as discussed above.

The use of device 10 assists the driving gluteal muscles of the thigh in activities such as jogging. At the same time, the controlled pressure against the posterior calf muscles relaxes and relieves fatigue in the leg muscles to permit persons otherwise unable to do so to enter into the highly desirable activities of jogging and the like.

Device 10 further cooperates with the tibialis anterior muscles in controlling the movement of the user's foot in the walking and jogging activities for further improved facilitated exercising of the user's lower limbs.

As discussed above, device 10 may be utilized as a relaxor device upon termination of the exercising activity so as to effectively minimize fatigue pain and the like and thereby further permit extended helpful and useful exercising by the user.

As device 10 is formed of simple overlapped fabric portions, the device may be worn under normal clothing, such as stockings. Further, as the device is formed of conventional elastic fabric and Velcro materials, the device may be suitably washed, as desired.

Device 10 is extremely simple of construction while yet providing the highly desirable muscle assisting and relaxing functioning discussed above. By extending healthful activities, such as jogging, to persons not normally capable of entering into such activities, the device provides a highly meritorious aid in increasing the health and wellbeing of a wide spectrum of society.

The foregoing disclosure of specific embodiments is illustrative of the broad inventive concepts comprehended by the invention.

I claim:

1. A device for assisting and relaxing a user's leg muscles in and after physical activities such as jogging, said device comprising:
    a strap member having a top end, a bottom end, and an elastic midportion having a width substantially the width of a user's heel;
    a first securing means extending from said top end and defining means for releasably encircling the user's leg adjacent the knee for securing said top end of the strap member thereto; and
    a second securing means extending from said bottom end and defining means for releasably encircling the user's foot for securing said bottom end of the strap member thereto with said midportion stretchably retained against the calf of the user's leg and said bottom end extending around the user's heel and underlying the arch of the user's foot for providing a supportive force on the user's leg during a physical activity such as jogging.

2. The device of claim 1 wherein said strap member includes means for selectively adjusting the length thereof.

3. The device of claim 1 wherein said strap member includes a plurality of portions, and means for adjustably connecting said portions in adjusted end-to-end relationship for adjusting the stretched condition of the strap member when the device is installed on the user's leg.

4. The device of claim 1 wherein said strap member includes a plurality of portions, and releasable self-holding fabric means on confronting portions of said strap member portions for adjustably connecting said portions in adjusted end-to-end relationship for adjusting the stretched condition of the strap member when the device is installed on the user's leg.

5. The device of claim 1 wherein said securing means include releasable self-holding fabric portions for adjustably securing the bands in said encircling disposition.

6. The device of claim 1 wherein each of said securing means comprises a pair of securing bands.

7. The device of claim 1 wherein said strap member comprises an elastic strap member.

8. The device of claim 1, wherein said first securing means includes a pair of securing band means, one of said band means being arranged to encircle the user's leg above the knee and the other of said band means being arranged to encircle the user's leg below the knee.

9. The device of claim 1 wherein said first securing means includes a pair of securing band means, one of said band means being arranged to encircle the user's leg above the knee and the other of said band means being arranged to encircle the user's leg below the knee, said band means comprising a pair of crossed elastic strips.

10. The device of claim 1 wherein said first securing means includes a pair of securing band means, one of said band means being arranged to encircle the user's leg above the knee and the other of said band means being arranged to encircle the user's leg below the knee, said band means comprising a pair of crossed elastic strips, said elastic strips including releasable self-holding fabric portions for adjustably securing the band means in said encircling disposition.

* * * * *